United States Patent [19]

Thieme et al.

[11] 4,251,539

[45] Feb. 17, 1981

[54] AMINO DERIVATIVES OF 3-ALKYL-5-(2-HYDROXYSTYRYL)-ISOXAZOLES

[75] Inventors: Peter C. Thieme, Wachenheim; Fritz-Frieder Frickel, Ludwigshafen; Hans Theobald, Limburgerhof; Albrecht Franke, Wachenheim; Dieter Lenke, Ludwigshafen; Josef Gries, Wachenheim, all of Fed. Rep. of Germany

[73] Assignee: BASF Aktiengesellschaft, Fed. Rep. of Germany

[21] Appl. No.: 30,927

[22] Filed: Apr. 17, 1979

[30] Foreign Application Priority Data

Apr. 29, 1978 [DE] Fed. Rep. of Germany ....... 2818999

[51] Int. Cl.³ .................... C07D 261/08; A61K 31/42
[52] U.S. Cl. .................... 424/272; 542/429; 542/455
[58] Field of Search ............ 424/272; 542/455, 429

[56] References Cited

U.S. PATENT DOCUMENTS

| 3,624,079 | 11/1971 | Lednicer | 542/455 |
| 3,836,671 | 9/1974 | Barrett et al. | 424/272 |
| 4,130,650 | 12/1978 | Müller et al. | 424/272 |

FOREIGN PATENT DOCUMENTS 2624918 12/1977 Fed. Rep. of Germany ........... 542/455

1307436 2/1973 United Kingdom ..................... 542/455

Primary Examiner—Arthur P. Demers
Attorney, Agent, or Firm—Keil & Witherspoon

[57] ABSTRACT

Alkylamino-propanol derivatives of 3-alkyl-5-(2-hydroxystyryl)-isoxazole, of the general formula

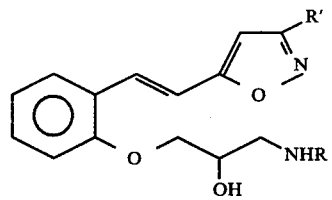

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl with 3 to 8 carbon atoms in the ring, the cycloalkyl rings being unsubstituted or mono- or di-substituted by alkyl of 1 to 3 carbon atoms, and R' is alkyl of 1 to 4 carbon atoms, and their addition salts with physiologically acceptable acids, their preparation, and pharmaceutical formulations which contain these compounds and which can be used as valuable drugs in the treatment of hypertonia, coronary diseases of the heart and cardiac arrhythmias.

16 Claims, No Drawings

AMINO DERIVATIVES OF 3-ALKYL-5-(2-HYDROXYSTYRYL)-ISOXAZOLES

The present invention relates to novel alkylaminopropanol derivatives of 3-alkyl-5-(2-hydroxystyrykl)-isoxazole, and their addition salts with physiologically acceptable acids, processes for their preparation and pharmaceutical formulations which contain these compounds and which can be used as drugs in the treatment of hypertonia, coronary diseases of the heart and cardiac arrhythmias.

We have found that compounds of the general formula (I)

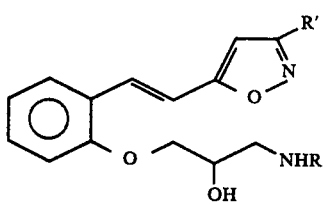

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl with 3 to 8 carbon atoms in the ring, the cycloalkyl rings being unsubstituted or mono- or di-substituted by alkyl of 1 to 3 carbon atoms, and R' is alkyl of 1 to 4 carbon atoms, and their addition salts with physiologically acceptable acids, exhibit valuable pharmacological properties.

Examples of straight-chain or branched alkyl R of 1 to 8 carbon atoms are methyl, ethyl, propyl, isopropyl, n-butyl, sec.-butyl, tert.-butyl, pent-2-yl, 2-methyl-but-2-yl, 3-methyl-but-2-yl, 3-methyl-pent-3-yl, 2,3-dimethyl-but-2-yl, 3-ethyl-pent-3-yl, 2,4-dimethyl-pent-3-yl and 2,4,4-trimethylpentyl, and examples of substituted alkyl radicals are 1-methoxy-prop-2-yl, 2-hydroxyeth-1-yl, 1-hydroxy-but-2-yl, 3-hydroxy-3-methyl-but-1-yl and 1-cyclopropyl-eth-1-yl.

Amongst the alkyl radicals, those which are of 3 to 6 carbon atoms and are branched at the carbon atoms in the α-position to the amino nitrogen are preferred. Preferred alkyl radicals are isopropyl and tert.-butyl.

Examples of alkenyl or alkynyl radicals R of 2 to 8 carbon atoms are prop-1-en-3-yl, but-3-yn-2-yl, 2-methyl-but-3-yn-2-yl and 3-ethyl-pent-1-yn-3-yl. Amongst these, 3-methyl-but-1-yn-3-yl is preferred.

Examples of cycloalkyl radicals are cyclopropyl, cyclobutyl, cyclopentyl, cycloheptyl and dimethylcyclohexyl, a particularly suitable alkyl substituent for the cyclic radicals mentioned being methyl. The preferred cycloalkyl radical is cyclopropyl.

Examples of straight-chain or branched alkyl radicals R' of 1 to 4 carbon atoms are methyl, ethyl, propyl, isopropyl, n-butyl, sec.-butyl and tert.-butyl. Amongst these, methyl and ethyl are preferred.

Accordingly, in addition to the compounds mentioned in the Examples, the following illustrate the compounds according to the invention: 3-methyl-5-[2-(2-hydroxy-3-amino-propoxy)-styryl]-isoxazole, 3-methyl-5-[2-(2-hydroxy-3-(butyl-2-amino)-propoxy)-styryl]-isoxazole, 3-methyl-5-[2-(2-hydroxy-3-(1-cyclopropylethyl-1-amino)-propoxy)-styryl]-isoxazole, 3-methyl-5-[2-(2hydroxy-3-(but-1ynyl-3-amino)-propoxy)-styryl]-isoxazole, 3-ethyl-5[2-(2-hydroxy-3-(2-methyl-but-1-ynyl-3-amino)-propoxy)-styryl]-isoxazole, 3-isopropyl-5-[2-(2-hydroxy-3-ethylamino-propoxy)-styryl]-isoxazole, 3-tert.-butyl-5-[2-(2-hydroxy-3-methylaminopropoxy)-styryl]-isoxazole, 3-n-butyl-5-[2-(2-hydroxy-3-isopropylamino-propoxy)-styryl]-isoxazole and 3-sec.-butyl-5-[2-(2-hydroxy-3-isopropylamino-propoxy)-styryl]-isoxazole.

The compounds according to the invention can be prepared by reacting a 3-alkyl-5-styryl-isoxazole of the general formula II

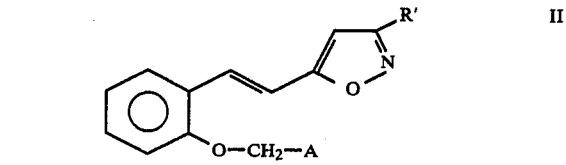

where A is

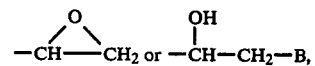

B being a nucleofugic leaving group, and R' has the meanings given for formula I, in the conventional manner with an amine of the general formula $H_2N-R$ where R has the meanings given for formula I, advantageously in a solvent and if appropriate in the presence of an acid-binding agent, and, if required, converting the resulting compound into an addition salt with a physiologically acceptable acid.

The leaving group B is preferably a halogen atom, especially chlorine, bromine or iodine. Further examples of nucleofugic leaving groups are aromatic or aliphatic sulfonic acid radicals, eg. the p-toluenesulfonic acid, p-bromobenzenesulfonic acid radical and methanesulfonic acid radical.

The reactions are carried out at from 10° to 120° C., ie. at room temperature or elevated temperatures, advantageously at from 50° to 120° C. The reactions may be carried out under atmospheric pressure or in a closed vessel under superatmospheric pressure, where necessary with heating to the stated temperature range.

In the case of volatile amines $H_2N-R$, in particular, it can be advantageous to carry out the reaction in a closed system, ie. an autoclave.

The starting compounds can be reacted directly, ie. without addition of a solvent or diluent. Advantageously, however, the reactions are carried out in the presence of an inert diluent or solvent, for example a lower alcohol of 1 to 4 carbon atoms, eg. methanol, ethanol or propanol, isopropanol or ethanol being preferred, a lower saturated dialkyl ether, dialkyl glycol ether or cyclic ether, eg. diethyl ether, 1,2-dimethoxyethane, tetrahydrofuran or dioxane, a benzene hydrocarbon, eg. benzene itself or an alkylbenzene, especially toluene or xylene, or an aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, dimethylsulfoxide or water, or a mixture of the said solvents.

An excess of the amine of the formula $H_2N-R$ may also serve as a suitable diluent or solvent.

Preferred solvents for the reaction of 3-alkyl-5-[2-(2,3-epoxy-propoxy)-styryl]-isoxazoles with an amine $R-NH_2$ are lower alcohols, especially ethanol or isopropanol, the reaction preferably being carried out at from 50° C. to 120° C. If appropriate, the reaction can be carried out in a closed vessel under pressure, especially if low-boiling amines are used. For the nucleophilic replacement of a radical B, preferred solvents are a lower aliphatic ketone, eg. acetone, methyl ethyl ketone or methyl isobutyl ketone, a cyclic aliphatic ether, especially tetrahydrofuran or dioxane, or a dialkylformamide, eg. dimethylformamide, and preferred temperatures are from 90° to 120° C. If appropriate, the reaction is carried out in the presence of a catalytic amount of sodium iodide or potassium iodide.

The starting compound of the formula II may also be a mixture of the epoxide with a halohydrin, since the industrial manufacture of the starting compounds under certain circumstances gives such mixtures.

In an advantageous embodiment of the nucleophilic replacement of the radical B by the amine used, the reaction is carried out in the presence of a base as the acid-binding agent. Preferred bases are alkali metal hydroxides, carbonates, bicarbonates or alcoholates, especially methylates and ethylates, or a tertiary organic amine, such as pyridine, or a trialkylamine, eg. trimethylamine or triethylamine. Amongst the alkali metal compounds, those of sodium and potassium are preferred. The base is used in stoichiometric amount or in slight excess. It is under certain circumstances advantageous to use an excess of the amine $H_2N-R$, employed for the reaction, so as to serve simultaneously as the acid-binding agent.

The time required to complete the reaction depends on the reaction temperature and is in general from 2 to 15 hours. The reaction product can be isolated in the conventional manner, for example by filtration or by distilling the diluent or solvent off the reaction mixture. The compound obtained is purified in the conventional manner, for example by recrystallization from a solvent, by conversion to an addition compound with an acid, or by column chromatography.

The starting compounds of the formula (II) can be obtained by alkylating a 3-alkyl-5-(2-hydroxy-styryl)-isoxazole (which is prepared, for example, in a Wittig reaction from a dialkyl-isoxazolyl-5-methylene-phosphonate and a salicylaldehyde having a protective group on the OH group, in accordance with our co-pending Patent Application P 28 18 998.2 of the same date), with an epihalohydrin or an α,ω-dihalopropan-2-ol. Suitable epihalohydrins are epichlorohydrin, epibromohydrin and epiiodohydrin and suitable, α,ω-dihalopropan-2-ols are in particular 1,3-dichloro-propan-2-ol and 1,3-dibromo-propan-2-ol.

The reaction of the 3-alkyl-5-(2-hydroxy-styryl)-isoxazoles to give the starting compounds of the formula II are advantageously carried out at from 0° to 120° C. and under atmospheric pressure or in a closed vessel under superatmospheric pressure. The reactions are advantageously carried out in an inert diluent or solvent, for example a lower aliphatic ketone, such as acetone, methyl ethyl ketone or methyl isobutyl ketone, a lower alcohol of 1 to 4 carbon atoms, eg. methanol, ethanol, propanol or butanol, a lower aliphatic or cyclic ether, eg. diethyl ether, tetrahydrofuran or dioxane, a dialkylformamide, eg. dimethylformamide or diethylformamide, or dimethylsulfoxide or hexamethylphosphorotriamide, or using excess alkylating agent as the diluent or solvent.

The reactions are preferably carried out in the presence of a base as the acid-binding agent. Suitable bases are alkali metal carbonates, bicarbonates, hydroxides, hydrides or alcoholates, especially of sodium or potassium, basic oxides, eg. aluminum oxide or calcium oxide, and organic tertiary bases, such as pyridine, piperidine or lower trialkylamines, eg. trimethylamine or triethylamine. The bases may be used in a catalytic amount relative to the alkylating agent employed, or in the stoichiometric amount or in slight excess.

Preferably, the 3-alkyl-5-(2-hydroxy-styryl)-isoxazoles are reacted with epibromohydrin or 1,2-dibromopropan-2-ol in a polar aprotic solvent, especially dimethylsulfoxide, in the presence of at least one mole equivalent of a base, especially sodium hydride, relative to the alkylating agent, at from 0° to 50° C.

Similarly to the process described in Liebigs Annalen der Chemie 1976, 221–224, for the reaction of phenol with 1,3-dichloro-propan-2-ol, 3-alkyl-5-(2-hydroxy-styryl)-isoxazoles can also be reacted with the equivalent amount of 1,3-dichloro-propan-2-ol in aqueous sodium hydroxide solution at about 50° C.

The starting compounds of the general formula II, in which A is the radical

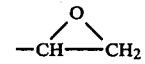

can also be obtained by reacting a methanephosphonic acid ester of the general formula VI

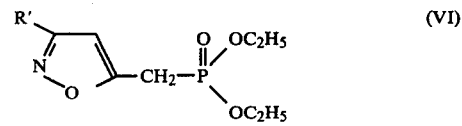

with the o-(2,3-epoxypropoxy)-benzaldehyde described in J. Chem. Soc. London 1974, 1,571–1,577.

Suitable reaction media for the reaction of o-(2,3-epoxypropoxy)-benzaldehyde with a phosphorane of the formula VI are inert organic solvents, for example a lower saturated dialkyl ether, dialkyl glycol ether or cyclic ether, eg. diethyl ether, 1,2-dimethoxyethane, tetrahydrofuran or dioxane, benzene or an alkylbenzene, eg. toluene or xylene, an aliphatic hydrocarbon, eg. hexane, heptane or octane, dimethylsulfoxide, dimethylformamide or a mixture of the said solvents. The reactions are carried out at from 0° C. to the boiling point of the solvents used, advantageously at room temperature, over from 1 to 48 hours, preferably from 1 to 16 hours, and advantageously in a nitrogen atmosphere. Suitable bases for this Wittig-Horner reaction are alkali metal hydrides, amides and alcoholates, especially those of sodium or potassium, sodium methylate being preferred.

According to a further method of preparation, the compounds of the general formula (I) are prepared in the conventional manner by alkylating a 3-alkyl-5-(2-hydroxy-styryl)-isoxazole of the formula III

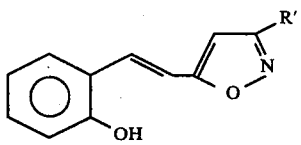 III, where R' has the above meanings, with a compound of the general formula IV or V

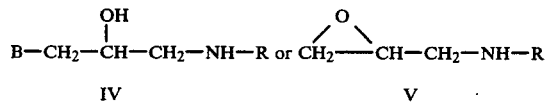

where B and R have the above meanings, advantageously in a solvent and, if appropriate, in the presence of an acid-binding agent, at from 40° to 120° C., and, if desired, the resulting compound is converted to an addition salt with a physiologically acceptable acid.

The above reaction can, for example, be carried out in accordance with the conditions described in Swiss Patent 451,115 or in German Laid-Open Application DOS No. 2,007,751.

The alkylation of a 3-alkyl-5-(2-hydroxystyryl)-isoxazole of the formula III with a compound of the formula IV is preferably carried out in the presence of an acid-binding agent, for example an alkali metal hydride, hydroxide, carbonate, bicarbonate or alcoholate, especially methylate or ethylate, or a tertiary organic amine, preferably pyridine, or a tertiary aliphatic amine, e.g. trimethylamine or triethylamine. Amongst the alkali metal compounds, those of sodium and potassium are preferred. The base is advantageously used in the stiochiometric amount or in slight excess. It is also possible, for example, to employ 2-hydroxy-styryl-isoxazole in the form of an alkali metal salt, for example the sodium salt or potassium salt.

The alkylation reactions are advantageously carried out in an inert diluent or solvent, for example a lower aliphatic alcohol of 1 to 4 carbon atoms, eg. methanol, ethanol, propanol, isopropanol or a butanol, or a lower aliphatic ketone, eg. acetone, methyl ethyl ketone or methyl isobutyl ketone, a cyclic ether, eg. tetrahydrofuran or dioxane, or a dialkylformamide, eg. dimethylformamide or diethylformamide, or dimethylsulfoxide. Advantageously, the reaction is accelerated, or terminated, by heating, for example at 40°-70° C. Amongst the solvents mentioned, the lower aliphatic ketones, dialkylformamides and dimethylsulfoxide are preferred.

The 3-alkyl-5-[2-(2-hydroxy-3-aminopropoxy)-styryl]-isoxazoles, ie. compounds of the formula I, where R is hydrogen, are advantageously obtained by the above processes from a compound of the formula II and ammonia. Preferably, the 3-alkyl-5-[2-(2,3-epoxypropoxy)-styryl]-isoxazole is reacted with an aqueous ammonia solution, or is reacted with gaseous ammonia in alcoholic solution, preferably in ethanol or isopropanol.

According to a further method of preparation, the compounds according to the invention can be obtained by reacting a methanephosphonic acid ester of the formula VI with a compound of the formula VII in the presence of a base and advantageously in the presence of a solvent in the conventional manner under the conditions of the Wittig-Horner reaction.

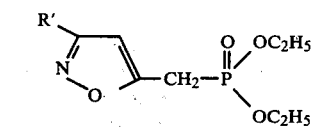 (VI)

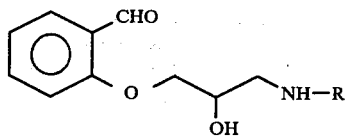 (VII)

These reactions can for example be carried out in accordance with the conditions described in German Laid-Open Application DOS No. 1,939,809. The preparation of the starting compounds of the general formula VI is described in German Laid-Open Applications DOS No. 2,549,962 and the preparation of the reactants in German Laid-Open Applications DOS No. 2,237,228 and DOS No. 2,327,270. The Wittig-Horner reactions are advantageously carried out in an inert diluent or solvent, for example a lower saturated dialkyl ether, dialkyl glycol ether or cyclic ether, eg. diethyl ether, 1,2-dimethoxyethane, tetrahydrofuran or dioxanes, benzene or an alkylbenzene, eg. toluene or xylene, an aliphatic hydrocarbon, eg. hexane, heptane or octane, dimethylsulfoxide or a mixture of the said solvents. The reactions are advantageously carried out at room temperature or by heating at 30°–80° C. Suitable bases are alkali metal hydrides, amides or alcoholates, especially those of sodium and potassium, as well as butyl-lithium and phenyl-lithium.

The novel compounds of the formula (I) possess a chirality center on carbon atom 2 of the aliphatic side chain and are obtained as racemates which can be separated into the optically active antipodes by conventional methods, for example by forming diastereomeric salts with optically active auxiliary acids, such as dibenzolytartaric acid, camphor-10-sulfonic acid, ditoluyltartaric acid or 3-bromo-camphor-8-sulfonic acid.

If required, the novel compounds obtained are converted to addition salts with physiologically acceptable acids. Examples of conventional physiologically acceptable inorganic or organic acids are, respectively, hydrochloric acid, hydrobromic acid, phosphoric acid and sulfuric acid, and oxalic acid, maleic acid, fumaric acid, lactic acid, tartaric acid, malic acid, citric acid, salicylic acid, adipic acid and benzoic acid; suitable acids may also be found in Fortschritte der Arzneimittelforschung, 10 (1966), 224–225, Birkhäuser Verlag, Basel and Stuttgart, and in Journal of Pharmaceutical Sciences, 66 (1977), 1–5.

The addition salts with acids are as a rule obtained in the conventional manner by mixing the free base, or a solution thereof, with the appropriate acid or a solution thereof in an organic solvent, for example a lower alcohol, eg. methanol, ethanol or propanol, or a lower ketone, eg. acetone, methyl ethyl ketone or methyl isobutyl ketone, or an ether, eg. diethyl ether, tetrahydrofuran or dioxane. Mixtures of the said solvents can also be used, to achieve better crystallization. In addition, pharmaceutically acceptable aqueous solutions of addition compounds of the aminopropanol derivatives of the general formula (I) with acids can be prepared by dissolving the free base of the general formula (I) in an aqueous solution of the acid.

The compounds according to the invention and their addition salts with physiologically acceptable acids exhibit valuable pharmacological properties. Pharmacodynamically, they can be characterized as highly active β-sympatholytic agents having an acute blood pressure-lowering or anti-hypertensive action. This type of action is unusual inasmuch as conventional β-sympatholytic agents, eg. propranolol, only exhibit an anti-hypertensive action on lengthy administration.

Because of the effects mentioned, the compounds can be used pharmacotherapeutically, especially for the treatment of hypertonia, of coronary diseases of the heart and of cardiac arrhythmias.

The pharmacodynamic properties were examined by the following methods:

1. β-Sympatholytic action on isoproterenol-induced tachycardia of narcotized cats.

The intravenous administration of 0.001 mg/kg of the β-sympathomimetic agent isoproterenol increases the pulse rate of mongrel cats (weight: 2–4 kg) under hexobarbital narcosis (200 mg/kg administered intramuscularly) by an average of 61 beats (40%).

β-Sympatholytic agents inhibit this increase in pulse rate specifically and as a function of the dose given. The substances tested are administered 10 minutes before the isoproterenol, to groups of from 3 to 5 cats per dose.

The ED 50% is the dose which is found to inhibit the isoproterenol-induced tachycardia by 50%.

2. Blood pressure-lowering action on narcotized rats.

To test the blood pressure-lowering action, the substances are administered intravenously to groups of from 3 to 5 male Sprague-Dawley rats (weight 230–280 g) under urethane narcosis (1.78 g/kg administered intraperitoneally).

The blood pressure in the carotid artery is measured by means of a Statham transducer.

The ED 20% is the dose which is found to lower the mean carotid artery pressure by 20%.

3. Anti-hypertensive action on spontaneously hypertonic rats.

The substances are administered orally to groups of 8 male spontaneously hypertonic Okamoto rats (weight 280–350 g). Before, and two hours after, the administration the systolic blood pressure is measured non-surgically on the rats' tails by means of piezoelectric crystal sensors.

The ED 20% is the dose which is found to lower the systolic pressure by 20%, taking into account the values found for untreated control animals.

4. Acute toxicity in mice

To determine the acute toxicity (LD 50), the substances are administered intraperitoneally to groups of 10 female MMRI mice (weight 19–20 g). The period of observation is 1 week.

The effective doses (see sections 1–3) were calculated from the linear relationships between the logarithms of the doses and of the action, with the aid of regression analysis. The LD 50 (see section 4) was determined with the aid of Probit analysis. The reference substance was the known β-sympatholytic agent propranolol.

As may be seen from Table 1, the β-sympatholytic activity of the Examples 1, 3, 6 and 13 is from 6.1 to 20 times greater than that of the known β-sympatholytic agent propranolol. The action of Example 5 is approximately equal to that of propranolol.

In addition to this effect, the substances according to the invention produce an acute lowering of the arterial blood pressure. After administration of 0.4 mg/kg of Example 3 to rats, a reduction in blood pressure averaging 20% is observed. In the same way, Examples 1, 5, 6 and 13 lower the blood pressure in doses of from 0.65 to 1 mg/kg (ED 20%). In contrast, propranolol increases the blood pressure of rats up to doses of 2.15 mg/kg. It is only the sub-lethal dose of 4.64 mg/kg which lowers the pressure by an average of 36%. About twice this dose (10 mg/kg) kills 2 out of 6 animals. After administration of 10 mg/kg of Example 3, 1 out of 6 animals dies. However, this dose is 25 times higher than the blood pressure-lowering dose (0.4 mg/kg).

As has been shown for Example 3, the substances also have a blood pressure-lowering action after oral administration to spontaneously hypertonic rats. 14.5 mg/kg lower the high blood pressure by an average of 20%. Propranolol is ineffective in this test, up to a dose of 100 mg/kg.

The lethal dose (LD 50 for intraperitoneal administration to mice) of Example 3 (123 mg/kg) is somewhat higher than that of propranolol (108 mg/kg), and that of Example 13 is more than twice as high as that of propranolol. Examples 1, 5 and 6 are of the same toxicity, or somewhat more toxic, than propranolol. However, in view of the high activity (compounds 1 and 6) and of the overall novel type of action, this finding is of no significance.

TABLE 1

| Example No. | β-Sympatholytic action (1) ED 50% | R.A. | Blood pressure-lowering action (2) ED 20% | Lethal character (4) LD 50 |
|---|---|---|---|---|
| 1 | 0.0077 | 14.3 | 0.65 | 108 |
| 3 | 0.0055 | 20.0 | 0.40 | 123 |
| 5 | 0.12 | 0.9 | 0.83 | 95 |
| 6 | 0.018 | 6.1 | 0.93 | 84 |
| 13 | 0.017 | 6.5 | 1.00 | 247 |
| Propranolol | 0.11 | 1.0 | (3) | 108 |

(1) Intravenous administration to cats under hexobarbital narcosis. ED 50% = dose, in mg/kg, which inhibits the isoproterenol-induced tachycardia by 50%. R.A. = relative activity. Propranolol = 1.00.
(2) Intravenous administration to rats under urethane narcosis. ED 20% = dose, in mg/kg, which lowers the blood pressure by 20%.
(3) Up to 2.15 mg/kg the blood pressure is increased by 11%; at 4.64 mg/kg it is lowered by 36%; at 10 mg/kg, 2 out of 6 animals died.
(4) Intraperitoneal administration to mice. LD 50 in mg/kg.

Accordingly, the present invention also relates to therapeutic agents or formulations which in addition to conventional excipients and diluents contain a compound of the formula (I) as the active ingredient, and to the use of the novel compounds for therapeutic purposes.

The therapeutic agents or formulations are prepared in the conventional manner with the conventional excipients or diluents and the conventional pharmaceutical auxiliaries, in accordance with the desired route of administration, and so as to provide a suitable dose.

The preferred formulations are those suitable for oral administration. Examples of these are tablets, film tablets, dragees, capsules, pills, powders, solutions or suspensions, or forms which exert a depot effect.

Of course, formulations for parenteral administration, eg. injection solutions, are also suitable. Suppositories are a further example of suitable formulations.

Appropriate tablets can be obtained, for example, by mixing the active ingredient with conventional auxiliaries, for example inert excipients, eg. dextrose, sugar, sorbitol, mannitol or polyvinylpyrrolidone, disintegrating agents, eg. corn starch or alginic acid, binders, eg.

starch or gelatin, lubricants, eg. magnesium stearate or talc, and/or agents added in order to achieve a depot effect, eg. carboxypolymethylene, carboxymethylcellulose, cellulose acetate-phthalate or polyvinyl acetate. The tablets can also consist of several layers.

Dragees may be produced by coating cores, prepared similarly to the tablets, with agents conventionally used in dragee coatings, for example collidone or shellac, gum arabic, talc, titanium dioxide or sugar. The dragee coating can also consist of several layers, and the auxiliaries mentioned above in connection with tablets can be used.

Solutions or suspensions containing the active ingredients according to the invention may in addition contain flavor improvers, eg. saccharin, cyclamate or sugar, and also, for example, flavorings such as vanillin or orange extract. Furthermore, they may contain suspending assistants, such as sodium carboxymethylcellulose, or preservatives, such as p-hydroxybenzoates. Capsules containing the active ingredient can be prepared, for example, by mixing the active ingredient with an inert excipient, such as lactose or sorbitol, and encapsulating the mixture in gelatin capsules.

Suitable suppositories can be prepared, for example, by mixing the active ingredient with suitable excipients, eg. neutral fats, polyethylene glycol or derivatives of these.

For man, a suitable single dose of the compounds according to the invention is from 1 to 100 mg, preferably from 3 to 50 mg.

Some compounds which warrant special mention because of their activity are 3-methyl-5-[2-(2-hydroxy-3-isopropylamino-propoxy)-styryl]-isoxazole, 3-methyl-5-[2-(2-hydroxy-3-tert.-butylamino-propoxy)-styryl]-isoxazole, 3-ethyl-5-[2-(2-hydroxy-3-tert.-butylamino-propoxy)-styryl]-isoxazole, 3-ethyl-5-[2-(2-hydroxy-3-cyclopropylamino-propoxy)-styryl]isoxazole and 3-methyl-5-[2-(2-hydroxy-3-(3-methyl-but-1-ynyl-3-amino)-propoxy)-styryl]-isoxazole.

The Examples which follow illustrate the invention.

PREPARATION OF INTERMEDIATES

Compound I: o-(α-Methoxy-ethoxy)-benzaldehyde (a) 610 g (5 moles) of salicylaldehyde are dissolved in 1.5 liters of xylene; 900 g (5 moles) of a 30% strength solution of NaOCH$_3$ in methanol are added dropwise to this solution at 40°–50° C. The mixture is then heated and the methanol is distilled off and is progressively replaced, in the reaction flask, by the same amount of xylene. Heating is continued until the xylene begins to distil off (about 130° C. at the distillation bridge). The suspension of the Na salt of the salicylaldehyde is then cooled to 60° C. and reacted further as described under (c).

(b) A pinch of hydroquinone is added to 200 ml of xylene, the mixture is cooled to from −20° to −30° C. and 290 g (5 moles) of vinyl methyl ether are condensed therein. 183 g (5 moles) of HCl gas are then introduced at −30° C., and the solution is allowed to stand so as to come to room temperature. The resulting solution of 1-chloroethyl methyl ether is reacted further as described under (c).

(c) The solution of 1-chloroethyl methyl ether, prepared as described under (b), is added dropwise to the solution, kept at 60° C., of the Na salt of salicylaldehyde (see (a)); the mixture is then stirred for about 1½ hours at 60° C., if necessary the pH is brought to 8–9 with 30% strength NaOCH$_3$ solution, and stirring is continued overnight at room temperature.

The sodium chloride which has precipitated is then filtered off and washed with xylene, and the xylene is distilled off on a rotary evaporator. The residue which is left is distilled through a column under 2 mm Hg. 690 g of o-(α-methoxyethoxy)-benzaldehyde, of boiling point 94°–96° C./2 mm Hg, are obtained.

Compound II:
(3-Methylisoxazol-5-yl)-methanephosphonic acid diethyl ester 445 g of 5-chloromethyl-3-methylisoxazole and 674 g of triethyl phosphite are slowly heated to 150° C. and left at this temperature for 4 hours. After distillation, 546 g (69% of theory) of (3-methylisoxazol-5-yl)-methanephosphonic acid diethyl ester of boiling point 118°–121° C./0.3 mm Hg are obtained. $^1$H-NMR spectrum (CHCl$_3$, with TMS as internal standard): τ=3.85 (d, J=3 Hz, 1H), 4.17 (m, J=8 Hz, 4H), 6.67 (d, J=22 Hz, 2H), 7.72 (s, 3H), 8.67 (t, J=8 Hz, 6H)

C$_9$H$_{16}$NO$_4$P (233.21)

calculated: C 46.35% H 6.91% N 6.01% P 13.28%.
found: C 45.9% H 7.0% N 6.0% P 13.0%.

Compound III:
(3-Ethylisoxazol-5-yl)-methanephosphonic acid diethyl ester 15 g of 5-chloromethyl-3-ethyl-isoxazole and 18 g of triethyl phosphite are slowly heated to 150° C. and left at this temperature for 2½ hours. After the mixture has cooled, it is distilled under reduced pressure. 18.2 g of (3-ethylisoxazol-5-yl)-methanephosphonic acid diethyl ester of boiling point 120°–121° C./0.2 mm Hg are obtained. Yield: 71.2%. $^1$H-NMR spectrum (CDCl$_3$, with TMS as internal standard): τ=3.85 (d, J=3 Hz, 1H), 4.17 (m, J=Hz, 4H), 6.60 (d, H=20 Hz, 2H), 7.35 (q, J=Hz, 2H), 8.50–8.93 (m, 9H)

C$_{10}$H$_{18}$NO$_4$P (247.23)

calculated: C 48.58% H 7.34% N 5.67% P 12.53%.
found: C 48.4% H 7.1% N 5.7% P 12.3%.

The following phosphonic acid esters were prepared by a similar method:

(3-isopropyl-isoxazol-5-yl)-methanephosphonic acid diethyl ester
Boiling point: 117°–122° C./0.3 mm Hg.
Yield 73%

(3-tert.-butyl-isoxazol-5-yl)-methanephosphonic acid diethyl ester
Boiling point: 126°–132° C./0.3 mm Hg.
Yield 88%

PREPARATION OF THE STARTING MATERIALS

EXAMPLE I

3-Methyl-5-(2-hydroxy-styryl)-isoxazole 8.8 g (0.2 mole) of a 55% strength sodium hydride suspension in paraffin oil are introduced into 100 ml of absolute dimethylsulfoxide. 47 g (0.2 mole) of diethyl(3-methyl-isoxazol-5-yl)-methylenephosphonate are added dropwise at room temperature. Stirring is continued for 30 minutes, after which 36 g (0.2 mole) of o-(1-methoxyethoxy)-benzaldehyde are added dropwise, whilst stirring, and then the reaction mixture is stirred at room temperature for 24 hours. Thereafter, it is poured onto 1 liter of ice water and extracted with three 80 ml portions of methylene chloride. The combined organic phases are dried with sodium sulfate and concentrated on a rotary evaporator. The oily residue is dissolved in 80 ml of methanol and 10 ml of water, 2 ml of 5 N HCl are added and stirring is continued for 10 minutes. An excess of water is then slowly added to the mixture until a precipitate separates out. The precipitate is filtered off, washed with water and recrystallized from ethanol. 19 g (47% of theory) of colorless crystals, melting point 236°–238° C.

$C_{12}H_{11}NO_2$ (201)

calculated: C 71.6 H 5.5 N 7.0. found: C 71.8 H 5.5 N 6.8.

EXAMPLE II

3-Ethyl-5-(2-hydroxy-styryl)-isoxazole

Using the method described in Example I, 6 g (0.02 mole) of diethyl-(3-ethyl-isoxazol-5-yl)-methylenephosphonate and 4.4 g (0.02 mole) of o-(1-methoxy-ethoxy)-benzaldehyde are reacted and the product is recrystallized from isopropanol. 1.7 g (32% of theory) of colorless crystals. Melting point 175°–176° C.

$C_{13}H_{13}NO_2$ (215)

Calculated: C 72.5 H 6.1 N 6.5. found: C 72.5 H 6.2 N 6.6.

EXAMPLE III

3-Isopropyl-5-(2-hydroxy-styryl)-isoxaole

Using the method described in Example I, 32 g (0.12 mole) of diethyl-(3-isopropyl-isoxazol-5-yl)-methylenephosphonate and 22 g (0.12 mole) of o-(1-methoxy-ethoxy)-benzaldehyde are reacted and the product is recrystallized from toluene. 20 g (73% of theory) of colorless crystals. Melting point 129°–133° C.

$C_{16}H_{15}NO_2$ (229)

calculated: C 73.3 H 6.6 N 6.1. found: C 73.7 H 6.7 N 5.8.

EXAMPLE IV 3-tert.-Butyl-5-(2-hydroxy-styryl)-isoxazole

Using the method described in Example I, 35 g (0.13 mole) of diethyl-(3-tert.-butyl-isoxazol-5-yl)-methylenephosphonate and 23 g (0.13 mole) of o-(1-methoxyethoxy)-benzaldehyde are reacted and the product is recrystallized from toluene. 24.8 g (78% of theory) of colorless crystals. Melting point 152°–155° C.

$C_{15}H_{17}NO_2$ (243)

calculated: C 74.0 H 7.0 N 5.8. found: C 73.4 H 7.3 N 5.5.

EXAMPLE V

3-Methyl-5-[2-(2,3-epoxypropoxy)-styryl]isoxazole 6.44 g of 55% strength sodium hydride in paraffin oil (0.15 mole) are introduced into 200 ml of absolute dimethylsulfoxide and 30 g (0.15 mole) of 3-methyl-5-(2-hydroxystyryl)-isoxazole, dissolved in 50 ml of dimethylsulfoxide, are added dropwise at room temperature. When the evolution of hydrogen has ceased, 20.2 g (0.15 mole) of epibromohydrin are added dropwise and the reaction mixture is stirred for 20 hours at room temperature. The mixture is then poured onto 1.5 liters of ice water and the solid precipitate is filtered off and recrystallized from isopropanol. 26.2 g (68% of theory) of colorless crystals, melting point 99°–100° C.

$C_{15}H_{15}NO_3$ (257)

calculated: C 70.0 H 5.9 N 5.4. found: C 70.0 H 5.9 N 5.5.

EXAMPLE VI

3-Ethyl-5-[2-(2,3-epoxypropoxy)-styryl]-isoxazole

This compound is prepared by the method described for Example V, from 5.1 g of 55% strength sodium hydride (0.116 mole), 25.0 g (0.116 mole) of 3-ethyl-5-(2-hydroxystyryl)-isoxazole and 15.9 g (0.116 mole) of epibromohydrin. The reaction mixture is poured into sodium chloride solution and extracted by shaking with diethyl ether. The ether solution is dried over anhydrous sodium sulfate, and concentrated. 29.2 g (93% of theory) of a colorless oil are obtained.

EXAMPLE VII

3-Isopropyl-5-[2-(2,3-epoxypropoxy)-styryl]-isoxazole

This compound is prepared by the method described for Example VI, from 3.4 g of 55% strength sodium hydride (0.078 mole), 18 g (0.078 mole) of 3-isopropyl-5-(2-hydroxystyryl)-isoxazole and 10.8 g (0.078 mole) of epibromohydrin. 21.5 g (97% of theory) of a colorless oil.

EXAMPLE VIII 3-tert.-Butyl-5-[2-(2,3-epoxypropoxy)-styryl]-isoxazole

This compound is prepared by the method described for Example VI, from 3.8 g of 55% strength sodium hydride (0.086 mole), 21 g (0.086 mole) of 3-tert.-butyl-5-(2-hydroxystyryl)-isoxazole and 11.8 g (0.086 mole) of epibromohydrin. 25.0 g (97% of theory) of a colorless oil.

EXAMPLE IX 1.0 g of 3-methyl-5-[2-(2,3-epoxypropoxy)-styryl]-isoxazole is dissolved in 20 ml of a 3 N solution of hydrogen chloride in ether and left to stand for 12 hours at room temperature. The resinous component formed is separated off and chromatographed on silica gel, using chloroform. The product eluates are evaporated to dryness under reduced pressure and the crude product is then recrystallized from an acetone/cyclohexane mixture. 3-Methyl-5-[2-(2-hydroxy-3-chloropropoxy)-styryl]-isoxazole which is pure according to NMR spectroscopy and has a melting point of 67°–68° C. is obtained. $^1$H-NMR spectrum (CDCl$_3$, TMS as internal standard). $\tau$=2.30, 3.15 (m, 6H), 3.92 (s, 1H), 5.60–5.92 (m, 3H), 6.24 (d, J=3.5 Hz, 2H), 6.77 (broad s, OH).

PREPARATION OF COMPOUNDS ACCORDING TO THE INVENTION

EXAMPLE 1

3-Methyl-5-[2-(2-hydroxy-3-isopropyl-aminopropoxy)-styryl]-isoxazole 3.4 g (0.013 mole) of 3-methyl-5-[2-(2,3-epoxypropoxy)-styryl]-isoxazole and 2.3 g (0.039 mole) of isopropylamine in 50 ml of isopropanol are refluxed for 8 hours. When the reaction solution has cooled, it is filtered, and concentrated on a rotary evaporator. 3.8 g of solid residue are obtained and are recrystallized from toluene, giving 2.4 g (58% of theory) of colorless crystals, melting point 106°–108° C.

$C_{18}H_{24}N_2O_3$ (316.4)

calculated: C 68.3 H 7.6 N 8.9. found: C 68.4 H 7.6 N 9.0.

EXAMPLE 2

3-Methyl-5-[2-(2-hydroxy-3-cyclopropylaminopropoxy)-stryryl]-isoxazole

This compound is prepared by the method described for Example 1 from 5.0 g (0.019 mole) of 3-methyl-5-[2-(2,3-epoxypropoxy)-styryl]-isoxazole and 1.21 g (0.2 mole) of cyclopropylamine. 2.4 g (40% of theory) of colorless crystals from toluene. Melting point 108°–109° C.

$C_{18}H_{22}N_2O_3$ (314.4)

calculated: C 68.8 H 7.1 N 8.9. found: C 68.8 H 7.0 N 8.9.

EXAMPLE 3

3-Methyl-5-[2-(2-hydroxy-3-tert.-butylaminopropoxy)-styryl]-isoxazole

This compound is obtained by the method described for Example 1 from 5.0 g (0.019 mole) of 3-methyl-5-[2-(2,3-epoxypropoxy)-styryl]-isoxazole and 1.56 g (0.2 mole) of tert.-butylamine. 3.1 g (48% of theory) of colorless crystals, melting point 83°–85° C.

$C_{19}H_{27}N_2O_3.0.5\ H_2O$ (339.4)

calculated: C 67.3 H 8.0 N 8.3. found: C 67.2 H 7.9 N 8.1.

30 g of crude 3-methyl-5-[2-(2-hydroxy-3-tert.-butylaminopropoxy)-styryl]-isoxazole are dissolved in a small amount of ethanol and a solution of hydrogen chloride in ether is added dropwise until the compound has precipitated completely. The precipitate of 3-methyl-5-[2-(2-hydroxy-3-tert.-butylaminopropoxy)-styryl]-isoxazole hydrochloride is filtered off, washed with dry ether, twice recrystallized from a methanol-ether mixture (1:1 by volume) and dried.

Yield: 33.8 g (79% of theory) of melting point 217° C.

$C_{19}H_{27}O_3N_2Cl$ (367)

calculated: C 62.2 H 7.4 N 7.6 Cl 9.7. found: C 62.1 H 7.3 N 7.7 Cl 9.8.

In the same way, a solution of fumaric acid in ether gives the neutral fumarate, melting point 188° C.

EXAMPLE 4

3-Ethyl-5-[2-(2-hydroxy-3-isopropylaminopropoxy)-styryl]-isoxazole

This compound is prepared from 7 g (0.026 mole) of 3-ethyl-5-[2-(2,3-epoxypropoxy)-styryl]-isoxazole and 2.4 g of isopropylamine (0.04 mole) in 100 ml of isopropanol. 8.1 g of an oil are obtained; this is dissolved in 100 ml of isopropanol and a solution of hydrogen chloride in ether is added. The crystals which have precipitated are filtered off and dried. 4.9 g (50% of theory), melting point 134°–135° C.

$C_{19}H_{25}ClN_2O_3$ (366.9)

calculated: C 62.7 H 7.4 N 7.6 Cl 9.7. found: C 61.9 H 6.9 N 7.7 Cl 9.6.

EXAMPLE 5

3-Ethyl-5-[2-(2-hydroxy-3-cyclopropylaminopropoxy)-styryl]-isoxazole 7 g (0.026 mole) of 3-ethyl-5-[2-(2,3-epoxypropoxy)-styryl]-isoxazole and 2.3 g of cyclopropylamine (0.04 mole) are reacted in 100 ml of isopropanol, by the method described for Example 1. 8.6 g of an oil are obtained, and this is freed from impurities on a 55×5 cm column of Silica gel 60 (0.063–0.20 mm) from Merck. The eluant is a 9:1 mixture of methylene chloride and methanol. The purity of the fractions is tested by thin layer chromatography. 3.2 g of an oil are obtained; this is dissolved in 40 ml of isopropanol plus a small amount of ether and precipitated with 1.1 g of fumaric acid dissolved in hot isopropanol. The crystals are filtered off and dried. 2.1 g (21% of theory), melting point 137°–139° C.

$C_{22}H_{26}N_2\ O_5$ (386.5) calculated: C 65.2 H 6.7 N 7.2. found: C 64.7 H 6.8 N 7.5.

EXAMPLE 6

3-Ethyl-5-[2-(2-hydroxy-3-tert.-butylaminopropoxy)-styryl]-isoxazole 7 g (0.026 mole) of 3-ethyl-5-[2-(2,3-epoxypropoxy)-styryl]-isoxazole and 3.0 g (0.04 mole) of tert.-butylamine are reacted by the method described for Example 4. 6.6 g (66% of theory), melting point 163°–164° C.

$C_{20}H_{29}ClN_2O_3$ calculated: C 63.1 H 7.7 N 7.3 Cl 9.3. found: C 62.9 H 7.5 N 7.2 Cl 9.2.

EXAMPLE 7

3-Isopropyl-5-[2-(2-hydroxy-3-isopropylaminopropoxy)-styryl]-isoxazole 7 g (0.025 mole) of 3-isopropyl-5-[2-(2,3-epoxypropoxy)-styryl]-isoxazole and 3 g (0.05 mole) of isopropylamine are reacted by the method described in Example 1.

5.9 g (68% of theory) of colorless crystals are obtained from toluene. Melting point 87°–88° C.

$C_{20}H_{28}N_2O_3$ (344.5) calculated: C 69.7 H 8.2 N 8.1. found: C 69.9 H 8.2 N 8.1.

EXAMPLE 8

3-Isopropyl-5-[2-(2-hydroxy-3-cyclopropylaminopropoxy)-styryl]-isoxazole 7 g (0.025 mole) of 3-isopropyl-5-[2-(2,3-epoxypropoxy)-styryl]-isoxazole and 3 g (0.05 mole) of cyclopropylamine are reacted by the method described in Example 5. 3.0 g (30% of theory) of colorless crystals are obtained as the fumurate. Melting point 148°–152° C.

$C_{22}H_{28}N_2O_5$ (400.5) calculated: C 66.0 H 7.0 N 7.0. found: C 65.7 H 6.8 N 7.0.

EXAMPLE 9

3-Isopropyl-5-[2-(2-hydroxy-3-tert.-butylaminopropoxy)-styryl]-isoxazole 7 g (0.025 mole) of 3-isopropyl-5-[2-(2,3-epoxypropoxy)-styryl]-isoxazole and 3.6 g (0.05 mole) of tert.-butylamine are reacted by the method described in Example 4. 5.8 g (59% of theory) of colorless crystals are obtained. Melting point 191°–193° C.

$C_{21}H_{31}ClN_2O_3$ (394.9) calculated: C 63.9 H 7.9 N 7.1 Cl 9.0. found: C 64.1 H 8.0 N 6.9 Cl 9.1.

EXAMPLE 10

3-tert.-Butyl-5-[2-(2-hydroxy-3-isopropylaminopropoxy)-styryl]-isoxazole 7 g (0.023 mole) of 3-tert.-butyl-5-[2-(2,3-epoxypropoxy)-styryl]-isoxazole and 2.8 g (0.05 mole) of isopropylamine are reacted by the method described in Example 5. 2.5 g (27% of theory) of colorless crystals are obtained as the fumarate. Melting point 192°–194° C.

$C_{25}H_{34}N_2O_5$ (474.6) calculated: C 66.3 H 7.6 N 6.7. found: C 66.5 H 7.8 N 6.6

EXAMPLE 11

3-tert.-Butyl-5-[2-(2-hydroxy-3-cyclopropylamino-propoxy)-styryl]-isoxazole 7 g (0.023 mole) of 3-tert.-butyl-5-[2-(2,3-epoxy-propoxy)-styryl]-isoxazole and 2.7 g (0.047 mole) of cyclopropylamine are reacted by the method described in Example 1. 5.8 g of an oil are obtained; this is dissolved in diethyl ether and precipitated with 2 g of oxalic acid dissolved in a small amount of ethanol. 2.7 g (26% of theory) of colorless crystals are obtained. Melting point 170°–174° C.

$C_{23}H_{30}N_2O_7$ (446.5) calculated: C 61.9 H 6.8 N 6.3. found: C 62.9 H 7.0 N 6.2.

EXAMPLE 12

3-tert.-Butyl-5-[2-(2-hydroxy-3-tert.-butylamino-propoxy)-styryl]-isoxazole 7 g (0.023 mole) of 3-tert.-butyl-5-[2-(2,3-epoxy-propoxy)-styryl]-isoxazole and 3.4 g (0.047 mole) of tert.-butylamine are reacted by the method described in Example 4. 6.8 g (72% of theory) of colorless crystals are obtained. Melting point 207°–208° C.

$C_{22}H_{33}ClN_2O_3$ (408.9) calculated: C 64.6 H 8.1 Cl 8.7 N 6.9. found: C 64.2 H 8.0 Cl 8.6 N 6.7.

EXAMPLE 13

3-Methyl-5-[2-(2-hydroxy-3-(3-methyl-but-1-ynyl-3-amino)-propoxy)-styryl]-isoxazole 5 g (0.019 mole) of 3-methyl-5-[2-(2,3-epoxypropoxy)-styryl]-isoxazole and 1.7 g (0.02 mole) of 3-methyl-3-amino-but-1-yne are reacted by the method described in Example 3 and the product is converted to the hydrochloride as described for Example 3. Yield: 3.5 g (49% of theory), melting point 191° C.

$C_{20}25N_2ClO_3$ (376.9) calculated: C 63.7 H 6.7 N 7.4 Cl 9.4. found: C 63.7 H 6.8 N 7.7 Cl 9.5.

EXAMPLE 14

3-Methyl-5-[2-(2-hydroxy-3-tert.-butylaminopropoxy)-styryl]-isoxazole hydrochloride 2.4 g of 3-methyl-5-[2-(2-hydroxy-3-chloropropoxy)-styryl]-isoxazole, 10 ml of tert.-butylamine and 50 ml of dioxane are heated for 10 hours at 100° C. in an autoclave. After distilling off the volatile constituents under reduced pressure, the very viscous crude product is partitioned between ether and 2 N sulfuric acid and the aqueous phase is cautiously rendered alkaline with 4 N sodium hydroxide solution and is finally extracted with ether. After drying the organic phase over sodium sulfate, the solvent is removed and the residue left is converted to 3-methyl-5-[2-(2-hydroxy-3-tert.-butylamino-propoxy)-styryl]-isoxazole hydrochloride, of melting point 216°–218° C., by the method described in Example 3.

Formulation Examples prepared in the conventional manner:

| 1. Tablets: | | |
|---|---|---|
| (a) | An active compound of the formula I | 5 mg |
| | Lactose | 200 mg |
| | Methylcellulose | 15 mg |
| | Corn starch | 50 mg |
| | Talc | 11 mg |
| | Magnesium stearate | 4 mg |
| | | 285 mg |
| (b) | An active compound of the formula I | 20 mg |
| | Lactose | 178 mg |
| | Avicel | 80 mg |
| | Polywachs 6000 | 20 mg |
| | Magnesium stearate | 2 mg |
| | | 300 mg |
| (c) | A compound of the formula I | 50 mg |
| | Polyvinylpyrrolidone (mean molecular weight 25,000) | 170 mg |
| | Polyethylene glycol (mean molecular weight 4,000) | 14 mg |
| | Hydroxypropylmethylcellulose | 40 mg |
| | Talc | 4 mg |
| | Magnesium stearate | 2 mg |
| | | 280 mg |

The active compound is moistened with a 10% strength aqueous solution of the polyvinylpyrrolidone, forced through a sieve of 1.0 mm mesh width and dried a 50° C. The granules thus obtained are mixed with polyethylene glycol (mean molecular weight 4,000), hydroxypropylmethylcellulose, talc and magnesium stearate and the mixture is pressed to give tablets each weighing 280 mg.

| 2. | Example of dragees: | |
|---|---|---|
| | A compound of the formula I | 3 mg |
| | Lactose | 90 mg |
| | Corn starch | 60 mg |
| | Polyvinylpyrrolidone | 6 mg |
| | Magnesium stearate | 1 mg |
| | | 160 mg |

The mixture of the active ingredient, lactose and corn starch is granulated by moistening with an 8% strength aqueous solution of the polyvinylpyrrolidone and forcing through a 1.5 mm sieve, and the granules are dried at 50° C. and then forced through a 1.0 mm sieve. The granules resulting from the last operation are mixed with magnesium stearate and molded into dragee cores. These cores are coated in the conventional manner with a shell consisting essentially of sugar and talc.

| 3. | Capsule formulation: | |
|---|---|---|
| | A compound of the formula I | 5.0 mg |
| | Magnesium stearate | 2.0 mg |
| | Lactose | 19.3 mg |
| 4. | Injection solution: | |
| | A compound of the formula I | 10 mg |
| | Sodium chloride | 9 mg |
| | Distilled water to make up to 1.0 ml | |

We claim:
1. A compound of the general formula I

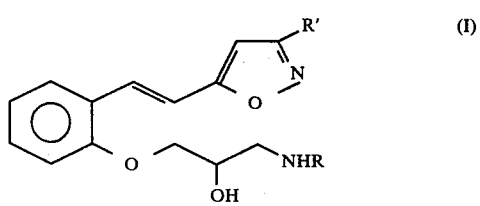

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl with 3 to 8 carbon atoms in the ring, the cycloalkyl rings being unsubstituted or mono- or di-substituted by alkyl of 1 to 3 carbon atoms, and R' is alkyl of 1 to 4 carbon atoms and its addition salts with acids.

2. A compound of the general formula I as claimed in claim 1, where R is isopropyl, tert.-butyl, cyclopropyl or 3-methyl-but-1-yn-3-yl and R' is alkyl of 1 to 4 carbon atoms.

3. 3-Methyl-5-[2-(2-hydroxy-3-isopropylamino-propoxy)-styryl]-isoxazole.

4. 3-Methyl-5-[2-(2-hydroxy-3-tert.-butylamino-propoxy)-styryl]-isoxazole.

5. 3-Ethyl-5-[2-(2-hydroxy-3-tert.-butylamino-propoxy)-styryl]-isoxazole.

6. 3-Ethyl-5-[2-(2-hydroxy-3-cyclopropylamino-propoxy)-styryl]-isoxazole.

7. 3-Methyl-5-[2-(2-hydroxy-3-(3-methyl-but-1-ynyl-3 amino-propoxy)-styryl]-isoxazole.

8. A therapeutic agent which comprises a therapeutic amount of a compound of the formula I as an active agent

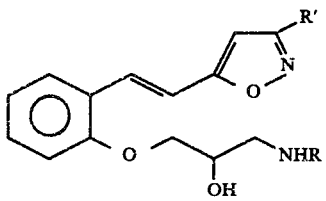

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl with 3 to 8 carbon atoms in the ring, the cycloalkyl rings being unsubstituted or mono- or di-substituted by alkyl of 1 to 3 carbon atoms, and R' is alkyl of 1 to 4 carbon atoms and of its addition salts with physiologically acceptable acids, said agent being combined with conventional excipients and diluents.

9. A therapeutic agent as claimed in claim 8, which comprises a compound of the formula I, where R is isopropyl, tert.-butyl, cyclopropyl or 3-methyl-but-1-yn-3-yl and R' is alkyl of 1 to 4 carbon atoms, or an addition salt thereof with a physiologically acceptable acid, as the active compound, together with conventional excipients and diluents.

10. A therapeutic agent as claimed in claim 8, which comprises 3-methyl-5-[2-(2-hydroxy-3-isopropylamino-propoxy)-styryl]-isoxazole, or an addition salt thereof with a physiologically acceptable acid, as the active compound, together with conventional excipients and diluents.

11. A therapeutic agent as claimed in claim 8, which comprises 3-methyl-5-[2-(2-hydroxy-3-tert.-butylamino-propoxy)-styryl]-isoxazole, or an addition salt thereof with a physiologically acceptable acid, as the active compound, together with conventional excipients and diluents.

12. A therapeutic agent as claimed in claim 8, which comprises 3-ethyl-5-[2-(2-hydroxy-3-tert.-butylamino-propoxy)-styryl]-isoxazole, or an addition salt thereof with a physiologically acceptable acid, as the active compound, together with conventional excipients and diluents.

13. A therapeutic agent as claimed in claim 8, which comprises 3-ethyl-5-[2-(2-hydroxy-3-cyclopropylaminopropoxy)-styryl]-isoxazole, or an addition salt thereof with a physiologically acceptable acid, as the active compound, together with conventional excipients and diluents.

14. A therapeutic agent as claimed in claim 8, which comprises 3-methyl-5-[2-(2-hydroxy-3-(3-methyl-but-1-ynyl-3-amino-propoxy)-styryl]-isoxazole, or an addition salt thereof with a physiologically acceptable acid, as the active compound, together with conventional excipients and diluents.

15. A method of lowering the blood pressure in humans which comprises administering to humans an effective amount of the compound of the formula I

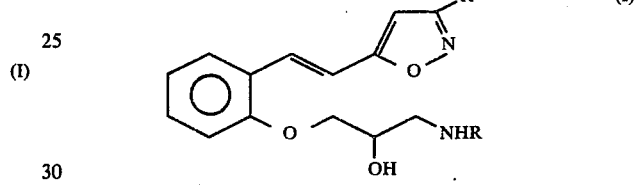

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl with 3 to 8 carbon atoms in the ring, the cycloalkyl rings being unsubstituted or mono- or di-substituted by alkyl of 1 to 3 carbon atoms, and R' is alkyl of 1 to 4 carbon atoms and of its addition salts with physiologically acceptable acids in single dosage units of from 1 to 100 mg.

16. A process for treating cardiac arrhythmias which comprises administering to humans an effective amount of the compound of the formula I

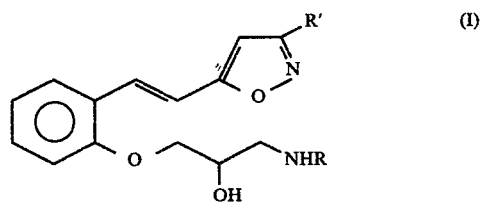

where R is hydrogen, alkyl of 1 to 8 carbon atoms, which is unsubstituted or substituted by hydroxyl, alkoxy of 1 to 3 carbon atoms or cycloalkyl with 3 to 8 carbon atoms in the ring, alkenyl or alkynyl of 2 to 8 carbon atoms, or cycloalkyl with 3 to 8 carbon atoms in the ring, the cycloalkyl rings being unsubstituted by mono- or di-substituted by alkyl of 1 to 3 carbon atoms, and R' is alkyl of 1 to 4 carbon atoms and of its addition salts with physiologically acceptable acids in single dosage units of from 1 to 100 mg.

* * * * *